United States Patent
Komatsubara et al.

(10) Patent No.: US 11,938,007 B2
(45) Date of Patent: Mar. 26, 2024

(54) DIAPER FOR PET

(71) Applicant: UNICHARM CORPORATION, Ehime (JP)

(72) Inventors: Daisuke Komatsubara, Kanonji (JP); Yumi Matsumoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 17/902,372

(22) Filed: Sep. 2, 2022

(65) Prior Publication Data

US 2022/0409444 A1    Dec. 29, 2022

Related U.S. Application Data

(63) Continuation of application No. PCT/JP2021/006042, filed on Feb. 18, 2021.

(30) Foreign Application Priority Data

Mar. 6, 2020  (JP) ................................. 2020-038779

(51) Int. Cl.
*A61F 13/494*  (2006.01)
*A61F 13/15*  (2006.01)
*A61F 13/49*  (2006.01)

(52) U.S. Cl.
CPC ...... *A61F 13/494* (2013.01); *A61F 13/49009* (2013.01); *A61F 2013/15186* (2013.01)

(58) Field of Classification Search
CPC ......... A61F 2013/15186; A61F 13/494; A01K 23/00
See application file for complete search history.

(56) References Cited

U.S. PATENT DOCUMENTS 9,750,230 B2 * 9/2017 Komatsubara ......... A01K 23/00
2014/0076246 A1 * 3/2014 Komatsubara ......... A01K 23/00
                                                                   119/869
(Continued)

FOREIGN PATENT DOCUMENTS

JP    2012205542 A    10/2012
JP    2013009657 A     1/2013
(Continued)

OTHER PUBLICATIONS

International Search Report issued in corresponding International Application No. PCT/JP2021/006042, dated Apr. 20, 2021, with translation (6 pages).

(Continued)

*Primary Examiner* — Michele Kidwell
(74) *Attorney, Agent, or Firm* — Osha Bergman Watanabe & Burton LLP

(57) ABSTRACT

A pet diaper includes: a top sheet; a back-surface sheet; an absorbent core disposed between the top sheet and the back-surface sheet; a tail hole portion including a hole body through which a tail of a pet is inserted; and an upright leak-proof gather including a rising portion including a contraction portion in which a leak-proof elastic member is disposed in a stretched state in a longitudinal direction, and a lateral fixed portion that is disposed away from the rising portion toward a lateral outer side and that functions as a rising fulcrum of the rising portion. The tail hole portion is disposed at a position that is away from an end edge of the absorbent core on the rear side toward the rear side. The contraction portion is disposed straddling a region between the tail hole portion and the absorbent core.

11 Claims, 4 Drawing Sheets

(56) References Cited

U.S. PATENT DOCUMENTS

| | | | | |
|---|---|---|---|---|
| 2015/0272713 A1* | 10/2015 | Komatsubara | ...... | A61F 13/5638 |
| | | | | 604/385.09 |
| 2016/0008183 A1* | 1/2016 | Komatsubara | ......... | A01K 23/00 |
| | | | | 604/385.09 |
| 2018/0317455 A1* | 11/2018 | Komatsubara | ............ | B32B 5/18 |
| 2022/0280355 A1* | 9/2022 | Komatsubara | ...... | A61F 13/5638 |

FOREIGN PATENT DOCUMENTS

| | | | |
|---|---|---|---|
| JP | 2014117173 A | 6/2014 |
| JP | 2014226110 A | 12/2014 |
| JP | 2016042793 A | 4/2016 |

OTHER PUBLICATIONS

Written Opinion issued in corresponding International Application No. PCT/JP2021/006042, dated Apr. 20, 2021 (4 pages).
Notice of Reasons for Refusal issued in corresponding Japanese Application No. 2020-038779 dated Jun. 28, 2022 (6 pages).
Decision to Grant for a Patent issued in corresponding Japanese Application No. 2020-038779 dated Sep. 6, 2022 (5 pages).
Office Action issued in corresponding Chinese Patent Application No. 202180018931.2, dated Mar. 24, 2023, with translation (13 pages).

\* cited by examiner

DIAPER FOR PET

BACKGROUND

Technical Field

The present invention relates to a pet diaper for pets, such as dogs and cats, to wear.

Description of Related Art

Patent Document 1 discloses a pet diaper to be put on pets such as dogs and cats. The pet diaper of Patent Document 1 has a tail hole for inserting the tail of a pet. In the vicinity of the tail hole of the diaper of Patent Document 1, an elastic member is provided which contracts the body of the diaper so as to close the tail hole.

Patent Document

Patent Document 1: Japanese Unexamined Patent Publication No. 2013-9657

In the pet diaper of Patent Document 1, the tail hole is easily deformed and closed by the contraction of the elastic member. Therefore, when a pet is in the pet diaper, the opening of the tail hole is easily fitted to the tail. However, when putting the pet diaper on a pet, sometimes it is difficult to properly insert the tail into the tail hole. In addition, because the tail hole is deformed and closed by the contraction of the elastic member, it is difficult to find out the tail hole. Therefore, some users have difficulty in noticing the presence of the tail hole and to properly insert the tail into the tail hole.

SUMMARY

A pet diaper according to one or more embodiments of the present invention may make it easy to properly insert the tail into a tail hole when putting the pet diaper on a pet.

A pet diaper according to one or more embodiments has a lateral direction that is arranged along a waistline direction of a pet and a longitudinal direction that is orthogonal to the lateral direction and extends in a direction connecting a stomach side and a rear side of the pet, the pet diaper comprising a main body portion that has a top sheet, a back-surface sheet, and an absorbent core arranged between the top sheet and the back-surface sheet. The main body portion has a tail hole (a tail hole portion) having a hole body portion (a hole body) through which a tail of a pet is capable of being inserted, and an upright leak-proof gather. The leak-proof gather has a rising portion that is capable of rising up, and a lateral fixed portion that is positioned away from the rising portion toward a lateral outer side and functions as a rising fulcrum of the rising portion. The rising portion has a contraction portion in which a leak-proof elastic member in a stretched state in the longitudinal direction is arranged. The tail hole is arranged at a position that is away from an end edge of the absorbent core toward the rear side, the end edge facing the rear side. The contraction portion is arranged straddling a region between the tail hole and the absorbent core.

DETAILED DESCRIPTION

(1) Outline of Embodiments

Figure 1:
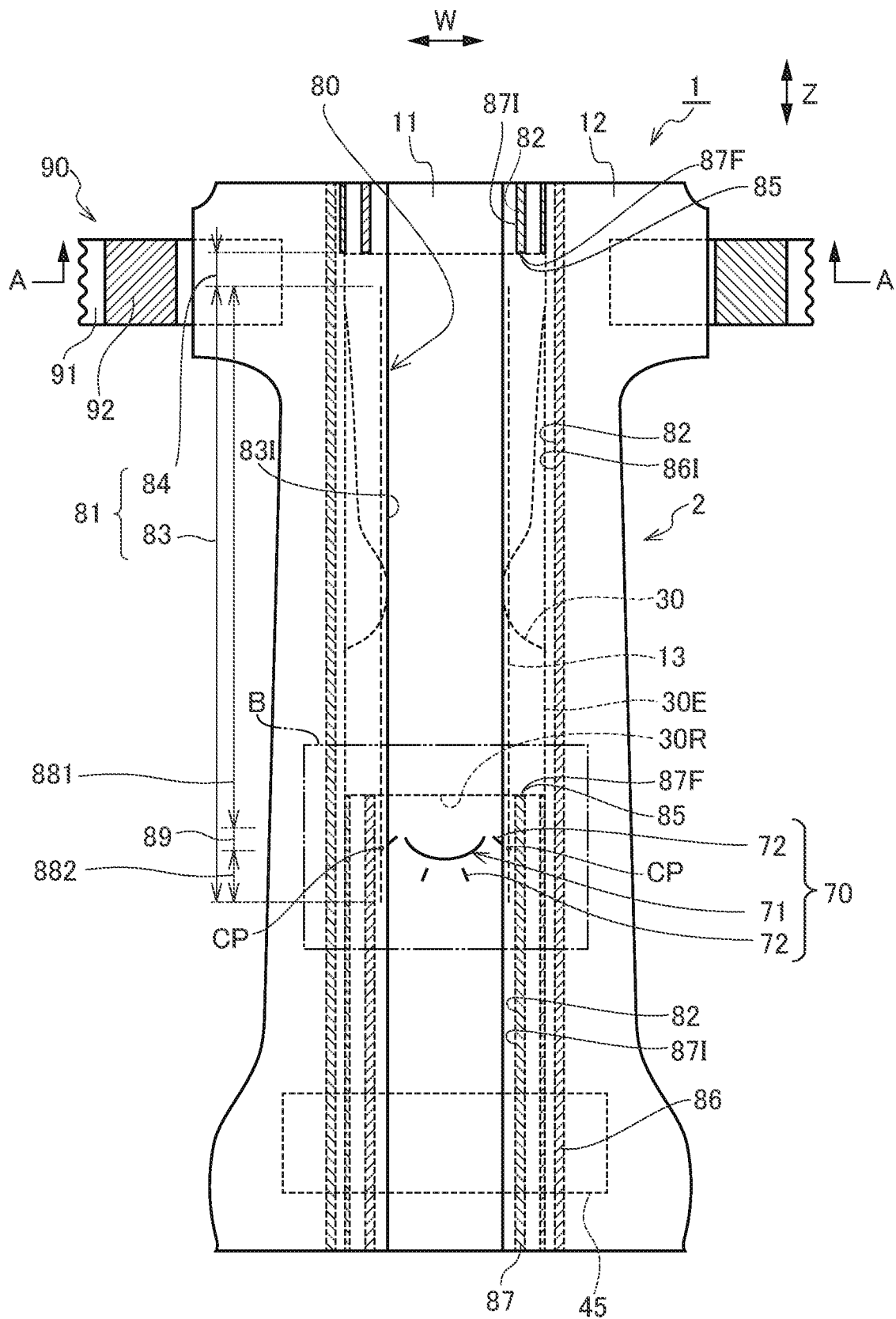
FIG. 1 is a plan view of a pet diaper according to one or more embodiments, seen from a skin facing side.

At least following matters will become clear with description of this specification and attached drawings.

A pet diaper according to one or more embodiments has a lateral direction that is arranged along a waistline direction of a pet and a longitudinal direction that is orthogonal to the lateral direction and extends in a direction connecting a stomach side and a rear side of the pet, the pet diaper comprising a main body portion that has a top sheet, a back-surface sheet, and an absorbent core arranged between the top sheet and the back-surface sheet. The main body portion has a tail hole having a hole body portion through which a tail of a pet is capable of being inserted, and an upright leak-proof gather. The leak-proof gather has a rising portion that is capable of rising up, and a lateral fixed portion that is positioned away from the rising portion toward a lateral outer side and functions as a rising fulcrum of the rising portion. The rising portion has a contraction portion in which a leak-proof elastic member in a stretched state in the longitudinal direction is arranged. The tail hole is arranged at a position that is away from an end edge of the absorbent core toward the rear side, the end edge facing the rear side. According to one or more embodiments, the region between the tail hole and the absorbent core contracts by the contraction portion, and the stomach-side end edge of the tail hole is pulled toward the absorbent core, which makes it easy for the tail hole to open. Accordingly, the user can easily notice the presence of the tail hole and properly insert the tail into the tail hole. Furthermore, the tail hole and the absorbent core are spaced apart in the longitudinal direction, and the contractive force generated by the contraction portion easily acts on the tail hole without being affected by the stiffness of the absorbent core. Therefore, when a pet is in the diaper, the opening of the tail hole is readily fitted to the tail.

According to one or more embodiments, the contraction portion may also be arranged in a hole side region that extends to the lateral outer side from the tail hole. According to one or more embodiments, because the contraction portion is arranged in the hole side region, the tail hole is deformed in a closing direction by the leak-proof gather. When putting the diaper on a pet, the user pulls the diaper in the longitudinal direction, which makes it easy for the user to notice the presence of the tail hole. In addition, because the tail hole is deformed in a closing direction and automatically opens when the diaper is put on a pet, the user can easily insert the tail into the tail hole when putting the diaper on a pet.

According to one or more embodiments, the contraction portion has a high contraction portion and a low contraction portion that has a weaker contractive force in the longitudinal direction compared to the high contraction portion, the low contraction portion may be arranged in at least a part of the hole side region, and the high contraction portion may be arranged on two longitudinal outer sides of the hole side region. According to one or more embodiments, the low contraction portion is arranged in the hole side region.

Therefore, the tail hole is not excessively deformed in a closing direction by the leak-proof gather, which makes it easy for the user to notice the presence of the tail hole when putting the diaper on a pet. In addition, because the tail hole is not excessively deformed in a closing direction, the user can easily insert the tail into the tail hole when putting the diaper on a pet. Furthermore, because the high contraction portion is arranged on two longitudinal outer sides of the hole side region, a force that contracts the low contraction portion in the longitudinal direction acts, which makes it easy for the opening of the tail hole to be fitted to the tail when a pet is in the diaper. Therefore, the hole side region is inhibited from excessively contracting in the longitudinal direction, and the opening of the tail hole is readily fitted to the tail when a pet is in the diaper.

According to one or more embodiments, the high contraction portion has a stomach-side high contraction portion that is away from the hole side region toward the stomach side and a rear-side high contraction portion that is away from the low contraction portion toward the rear side, and the length of the stomach-side high contraction portion in the longitudinal direction may be greater than the length of the rear-side high contraction portion in the longitudinal direction. Urine is more likely to be discharged to the region on the rear side of the tail hole than to the region on the stomach side of the tail hole. In a case where the stomach-side high contraction portion is long enough in the longitudinal direction, the region on the stomach side of the tail hole is provided with a long contraction portion, which makes it possible to suppress lateral leakage of a body fluid. Incidentally, a rear-side high contraction portion is also arranged in the region on the rear side of the tail hole. The rear-side high contraction portion makes the diaper fitted well to the rear side. Therefore, the entire diaper can cover the pet's body, which makes it possible to suppress leakage.

According to one or more embodiments, in the aforementioned pet diaper that is in a stretched state, the lateral fixed portion in the hole side region may be positioned away from the lateral fixed portion, which is in a region that is away from an end edge of the absorbent core on the rear side toward the stomach side, toward a lateral inner side. The absorbent core is arranged in a region that is away from the rear-side end edge of the absorbent core toward the stomach side. Because the lateral fixed portion in this region is positioned relatively on the lateral outer side, the rising portion on the sides of the absorbent core can be high enough, which makes it possible to suppress lateral leakage. In addition, because the lateral fixed portion in the hole side region is positioned relatively on the lateral inner side, the rising portion on the sides of the tail hole is inhibited from rising too high. Therefore, the tail hole is inhibited from being excessively deformed by the contraction of the rising portion when the diaper is put on a pet, which makes it easy to insert the tail into the tail hole when putting the diaper on a pet.

According to one or more embodiments, the leak-proof elastic member is cut at the low contraction portion, but is not cut at the high contraction portion and is continuously arranged. According to one or more embodiments, cutting the leak-proof elastic member makes it possible to easily provide the low contraction portion.

According to one or more embodiments, the leak-proof gather has the leak-proof elastic member and a leak-proof sheet to which the leak-proof elastic member is joined, and the leak-proof sheet may be cut at the low contraction portion together with the leak-proof elastic member. According to one or more embodiments, the leak-proof sheet is cut at the low contraction portion. Therefore, the user can easily recognize the cutting position of the leak-proof sheet by seeing the pet diaper from the outside and can easily notice the position or presence of the low contraction portion.

According to one or more embodiments, the cutting position of the leak-proof elastic member may be arranged on the stomach side with respect to the longitudinal center of the hole side region. The region on the stomach side with respect to the longitudinal center of the hole side region can be inhibited from excessively contracting by the influence of the cut leak-proof elastic member. Therefore, when the diaper is put on a pet, the tail hole is inhibited from being excessively deformed within the entire hole side region, which makes it easy to obtain an effect of more easily inserting the tail into the tail hole when putting the diaper on a pet.

According to one or more embodiments, the tail hole has the hole body portion and a notch portion that is a portion where the top sheet and the back-surface sheet can be torn off and is for enlarging the dimension of the hole body portion, and the low contraction portion may be arranged in a region that extends to the lateral outer side from the hole body portion. According to one or more embodiments, the hole body portion is not excessively deformed in a closing direction by the contraction of the leak-proof gather, which makes it easy for the user to notice the presence of the hole body portion when putting the diaper on a pet. In addition, because the hole body portion is not excessively deformed in a closing direction, it is easy to insert the tail into the tail hole when putting the diaper on a pet.

According to one or more embodiments, in the pet diaper that is in a stretched state, the leak-proof gather may be arranged in a region that overlaps the notch portion but does not overlap the hole body portion. According to one or more embodiments, the hole body portion is unlikely to be covered with the leak-proof gather, which makes it easy to secure visibility of the hole body portion. As a result, the user can easily notice the presence of the tail hole.

(2) Configuration of Pet Diaper

Hereinafter, a pet diaper according to one or more embodiments will be described with reference to the drawings. It should be noted that, in the following description of the drawings, identical or similar portions will be given identical or similar reference signs. Here, the drawings are schematic views, and attention needs to be paid to the fact that the ratios between individual dimensions and the like are different from actual ones. Therefore, specific dimensions and the like need to be determined with reference to the following description. In addition, there may be a portion where the relationship or ratio between dimensions does not match between drawings.

Figure 2:
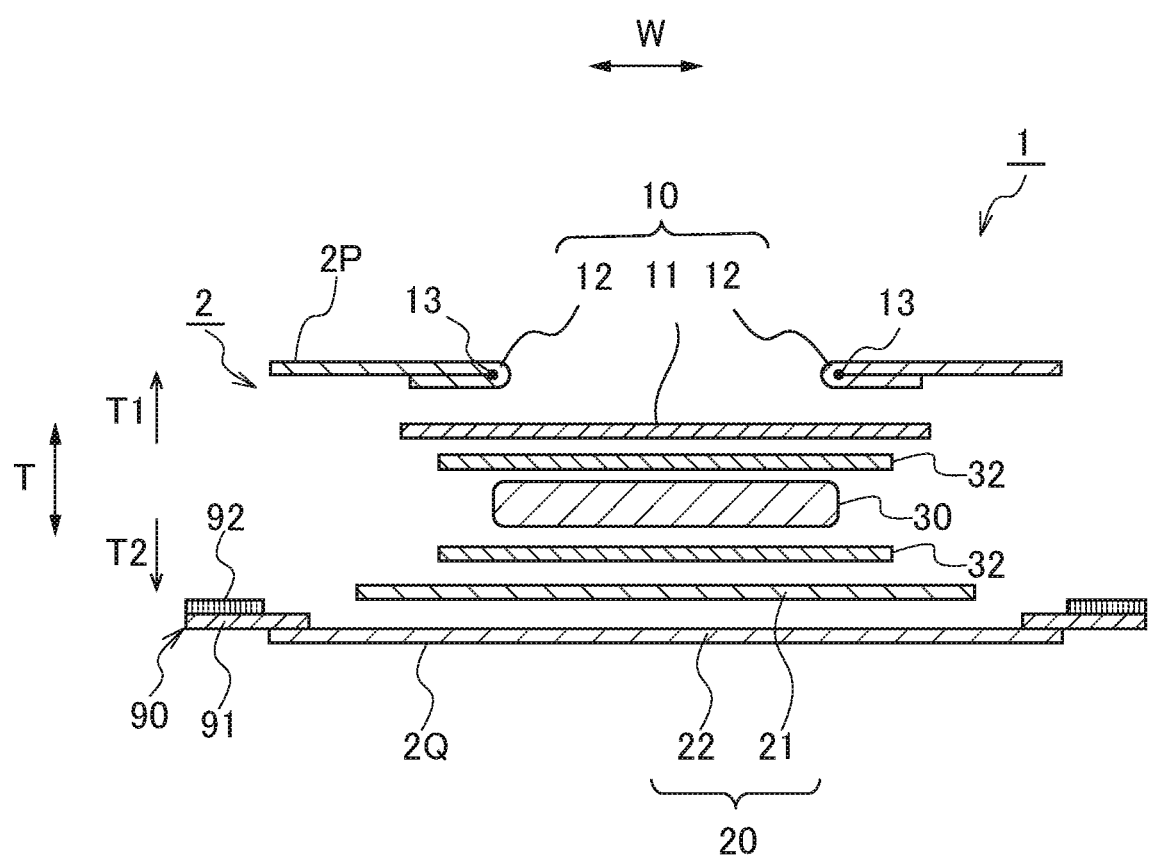
FIG. 2 is a schematic cross-sectional view of the pet diaper taken along a line A-A shown in FIG. 1.
Figure 3:
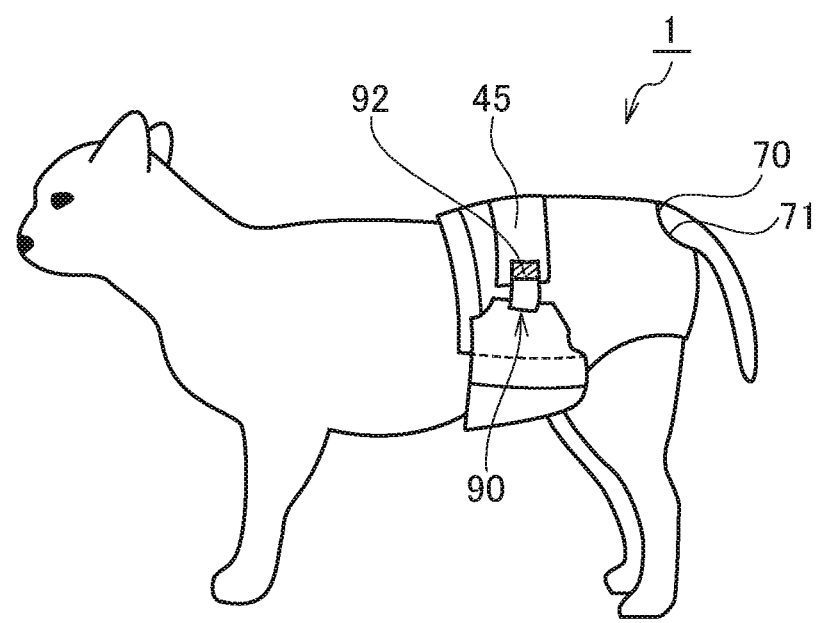
FIG. 3 is a view schematically showing the pet diaper according to one or more embodiments that is worn by a pet.
Figure 4:
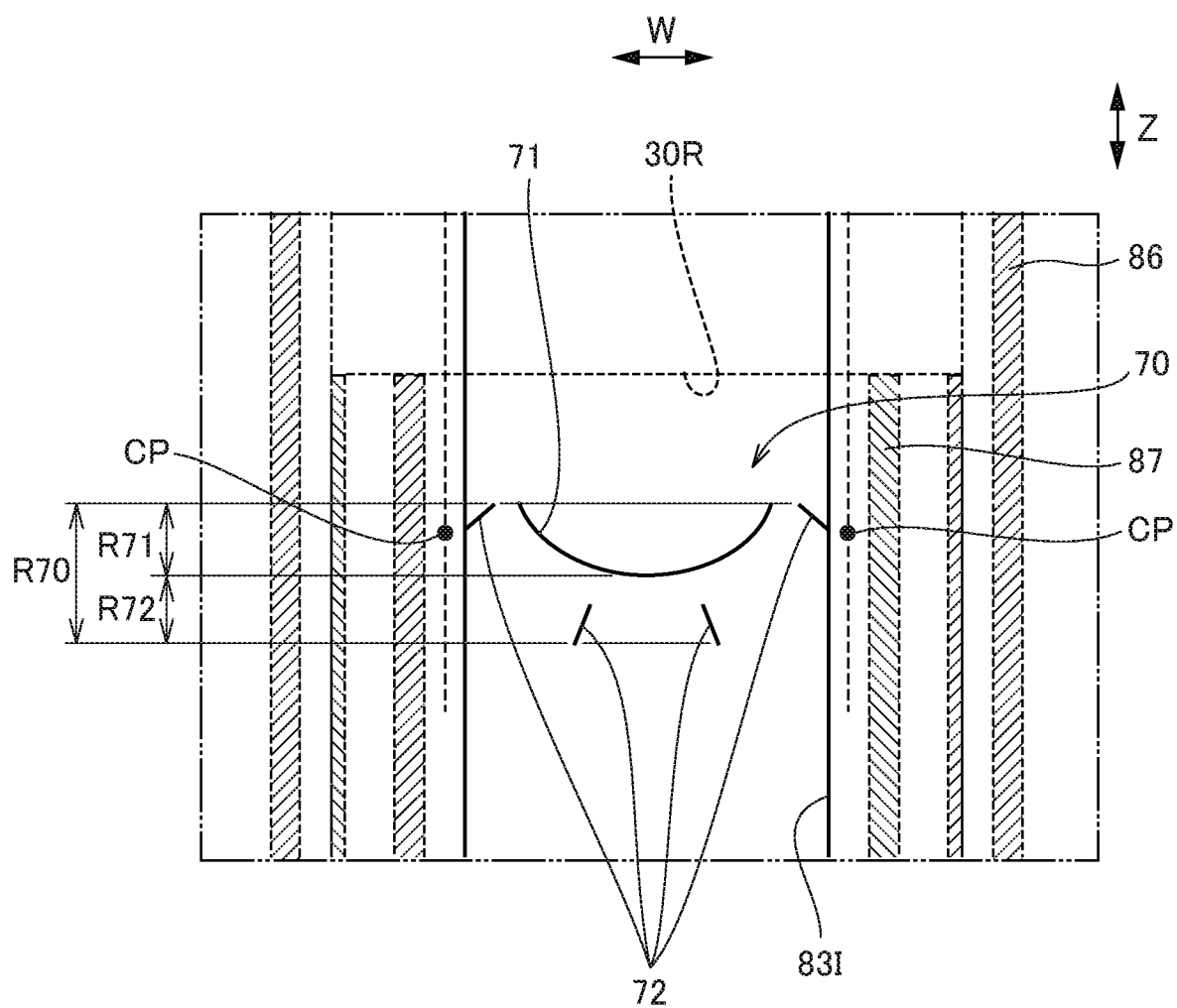
FIG. 4 is an enlarged plan view of part B shown in FIG. 1.

FIG. 1 is a plan view of a pet diaper according to one or more embodiments, seen from a top surface side T1. FIG. 2 is a schematic cross-sectional view of the pet diaper taken along a line A-A shown in FIG. 1. FIG. 1 and FIG. 2 show a pet diaper 1 in a stretched state where the diaper is stretched until no wrinkles are formed. Unless otherwise specified, the positional relationship in the following description is a positional relationship in a stretched state. In the cross-sectional view shown in FIG. 2, for the convenience of description, each member is illustrated as being spaced apart from each other in a thickness direction T. However, in an actual product, the members are in contact with each other in the thickness direction T. FIG. 3 is a view schematically showing the pet diaper worn by a pet. FIG. 4 is an enlarged plan view of part B shown in FIG. 1. A pet diaper 1 is a diaper used for pets such as dogs and cats.

The pet diaper 1 has a lateral direction W arranged along a waistline direction of a pet, a longitudinal direction Z orthogonal to the lateral direction W, and a thickness direction T orthogonal to the lateral direction W and the longitudinal direction Z. The longitudinal direction Z extends in a direction connecting the stomach side and the rear side of a pet. The thickness direction T extends to a top surface side T1 that comes into contact with a pet when a pet is in the diaper and a back surface side T2 that is exposed to the outside when a pet is in the diaper. As shown in FIG. 3, the pet diaper according to one or more embodiments is put on so as to cover the region ranging from the stomach side to back side of a pet through the crotch.

The pet diaper 1 may have a main body portion 2 and a fastening tape 90. The main body portion 2 has at least a top sheet 10, a back-surface sheet 20, and an absorbent core 30. The top sheet 10 is arranged on an inner surface (surface on the top-surface side) 2P of the main body portion 2 that is brought into contact with a pet. The top sheet 10 has liquid permeability that enables a body fluid to permeate toward the absorbent core 30. The top sheet 10 may have a center sheet 11 that is positioned at the center in the longitudinal direction Z and covers the absorbent core 30, and a side sheet 12 that covers two side portions of the center sheet 11 in the lateral direction W. As shown in FIG. 2, the side sheet 12 may be folded. Specifically, the side sheet 12 is folded back toward the back surface side T2 at the inner edge of the side sheet 12 in the lateral direction W. A leak-proof elastic member 13 stretched in the longitudinal direction Z may be arranged between the side sheets 12 folded back. The side sheet 12 and the leak-proof elastic member 13 may configure a leak-proof gather 80. The side sheet 12 configures the leak-proof sheet of the present invention. The leak-proof gather 80 is an upright gather positioned closer to the top side than the absorbent core 30. The leak-proof gather 80 will be specifically described later.

The absorbent core 30 is arranged between the top sheet 10 and the back-surface sheet 20. The absorbent core 30 is a laminate of absorbent materials such as pulp. As shown in FIG. 2, a core wrap 32 that covers the absorbent core 30 may be provided. The absorbent core 30 is arranged at a position that is away from two end edges of the main body portion 2 toward the inner side in the lateral direction W. That is, the length of the absorbent core 30 in the lateral direction W is smaller than the length of the main body portion 2 in the lateral direction W. The absorbent core 30 is arranged at the center of the main body portion 2 in the lateral direction W, and is not provided in the outer side portion of the main body portion 2 in the lateral direction W. Furthermore, the absorbent core 30 may be arranged at a position that is away from two end edges of the main body portion 2 toward the inner side in the longitudinal direction Z. That is, the length of the absorbent core 30 in the longitudinal direction Z may be smaller than the length of the main body portion 2 in the longitudinal direction Z. The absorbent core 30 may be arranged at the center of the main body portion 2 in the longitudinal direction Z, and may not be provided in the outer side portion of the main body portion 2 in the longitudinal direction Z. The absorbent core 30 may be spaced apart from the tail hole 70, which will be described later, in the longitudinal direction Z, and may be positioned away from the tail hole 70 toward the stomach side.

The back-surface sheet 20 is arranged on an outer surface (surface on the back-surface side) 2Q of the main body portion 2 that is positioned on the outer side when a pet is in the diaper. The back-surface sheet 20 may have a liquid-impermeable back-surface film 21 and a back-surface nonwoven fabric 22 positioned on a side closer to the back surface than the back-surface film 21. In a modified example, the back-surface sheet may have a liquid-impermeable back-surface film and a back-surface nonwoven fabric positioned on a side closer to the inner surface than the back-surface film 21. The length of the back-surface film 21 in the lateral direction W may be smaller than the length of the back-surface nonwoven fabric 22 in the lateral direction W. That is, the back-surface nonwoven fabric 22 may further extend than the back-surface film 21 toward two sides in the lateral direction W.

In one end portion (stomach-side end portion) of the main body portion 2 in the longitudinal direction Z, the fastening tape 90 extends further toward two outer sides in the lateral direction W than the main body portion 2. More specifically, the fastening tape 90 extends further toward the outer side in the lateral direction W than the end edge of the main body portion 2 in the lateral direction W. The fastening tape 90 may have a base sheet 91 that is joined to the main body portion 2, and a joining portion 92 that is provided on the base sheet 91 and capable of being joined to an outer surface 2Q of the main body portion 2. The joining portion 92 is arranged on a surface of the fastening tape 90, the surface being on the top surface side T1. The joining portion 92 may be a mechanical fastener and is configured to be joinable to a target portion 45 provided on the outer surface 2Q of the main body portion 2. It should be noted that, in a modified example, the main body portion 2 may not include the target portion 45, and the joining portion 92 may be configured so as to be joined to the back-surface sheet 20 of the main body portion 2 on the outer surface 2Q side. In the present invention, an end portion is a portion that occupies a certain region including end edges.

The main body portion 2 may be provided with the tail hole 70. The tail hole 70 may have the hole body portion 71 through which the tail of a pet can be inserted. In the pet diaper that is not yet used, the top sheet 10 and the back-surface sheet 20 in the hole body portion 71 are cut. When the diaper having the tail hole 70 is put on a pet so that the buttocks and back of the pet are covered with the rear-side end portion of the main body portion 2, the pet's tail may be inserted into the hole body portion 71 of the tail hole 70. The hole body portion 71 may be a semicircular notch. The hole body portion 71 may be a continuous notch or may be a constituent such as a perforation where the top sheet 10 and the back-surface sheet 20 can be torn off. The tail hole 70 may have a notch portion 72 for enlarging the dimension of the hole body portion 71. The notch portion 72 may be a constituent such as a perforation where the top sheet 10 and the back-surface sheet 20 can be torn off. The dimension of the hole body portion 71 can be adjusted according to the type and growth process of a pet. In the pet diaper that is not yet used, not the entirety of the notch portion 72, but a part of the notch portion 72 is cut. In one or more embodiments, two notch portions 72 are provided on each of the left and right sides of the center of the tail hole 70 in the lateral direction W. In a modified example, one notch portion 72 may be provided on each of the left and right sides of the center of the tail hole 70 in the lateral direction W, or a configuration may be adopted in which two or more notch portions 72 are provided so that the dimension of the tail hole 70 can be adjusted in multiple stages. The hole body portion 71 may be spaced apart from the absorbent core 30 in the longitudinal direction Z. The stomach-side end edge of the hole body portion 71 may be arranged at a position that is away from the rear-side end edge of the absorbent core 30 toward the rear side.

For example, the pet diaper 1 can be put on a pet by a method of bringing the diaper into contact with the rear side of a pet and then bringing the diaper into contact with the stomach side of the pet. Specifically, the pet's tail is slid through the tail hole 70 toward the back surface side T2 of the diaper. In this state, the stomach-side end portion (the end portion on the side provided with the joining portion 92) of the main body portion 2 is brought into contact with the pet's stomach. Then, in a state where the center of the main body portion 2 in the longitudinal direction Z is being brought into contact with the pet's urination opening, the buttocks and back of the pet are covered with the rear-side end portion of the main body portion 2. Next, the joining portion 92 is pulled toward the rear of the pet, and the joining portion 92 is fastened to the outer surface of the target portion 45 of the main body portion 2. The pet diaper can also be put on a pet by a method of bringing the diaper into contact with the stomach side of a pet and then bringing the diaper into contact with the rear side of the pet. Specifically, the stomach-side end portion (the end portion on the side provided with the joining portion 92) of the main body portion 2 is brought into contact with the pet's stomach. At this time, the rear-side end portion of the main body portion 2 is passed between two legs of the pet and left to extend toward the rear side of the pet. Then, in a state where the center of the main body portion 2 in the longitudinal direction Z is being brought into contact with the pet's urination opening, the pet's tail is slid through the tail hole 70 toward the back surface side T2 of the diaper. The buttocks and rear of the pet are covered with the rear-side end portion of the main body portion 2. Next, the joining portion 92 is pulled toward the rear of the pet, and the joining portion 92 is fastened to the outer surface of the target portion 45 of the main body portion 2. By the method described above, the pet diaper 1 can be put on a pet so that the diaper covers the stomach, back, and crotch of the pet as shown in FIG. 3. That is, the pet diaper 1 is worn so as to cover the region ranging from the stomach side to rear side of the pet through the crotch.

Next, the leak-proof gather 80 will be described. The main body portion 2 has the leak-proof gather 80. The leak-proof gather 80 has the leak-proof elastic member 13 and the side sheet (leak-proof sheet) 12 to which the leak-proof elastic member 13 is joined. The leak-proof gather 80 may have a rising portion 81 that is capable of rising up, a lateral fixed portion 82 that is positioned away from the rising portion 81 toward the outer side in the lateral direction W and functions as a rising fulcrum of the rising portion 81, and a longitudinal fixed portion 85 that is positioned away from the rising portion 81 toward the outer side in the longitudinal direction Z and functions as a rising fulcrum of the rising portion 81. The rising portion 81 is a portion where the side sheet 12 is not fixed to the center sheet 11. The rising portion 81 is a concept including a contraction portion 83 in which the leak-proof elastic member 13 in a stretched state is arranged and which contracts at least in the longitudinal direction Z and a non-contraction portion 84 in which the leak-proof elastic member 13 in a non-stretched state is arranged and which substantially does not contract in the longitudinal direction Z. For the convenience of description, FIG. 1 illustrates the leak-proof elastic member 13 fixed in a stretched state but does not illustrate the leak-proof elastic member arranged in a non-stretched state.

The lateral fixed portion 82 is a fixed portion adjacent to the rising portion 81 in the lateral direction W. In a case where a plurality of fixed portions is provided in rows at a position away from the rising portion 81 toward the outer side in the lateral direction W, the innermost fixed portion in the lateral direction W configures the lateral fixed portion 82. The fixed portion of one or more embodiments has a first fixed portion 86 and a second fixed portion 87 that is positioned away from the first fixed portion 86 toward the inner side in the lateral direction W. The first fixed portion 86 is arranged in the entire region of the diaper in the longitudinal direction Z. The second fixed portion 87 is arranged at the respective positions away from the rising portion 81 toward the outer side in the longitudinal direction Z. In the region between the second fixed portions 87 in the longitudinal direction Z, an inner edge 861 of the first fixed portion 86 configures the lateral fixed portion 82. In a region where the second fixed portion 87 is arranged in the longitudinal direction Z, an inner end edge 87F of the second fixed portion 87 in the longitudinal direction Z configures the longitudinal fixed portion 85, and an inner edge 871 of the second fixed portion 87 configures the lateral fixed portion 82. Therefore, in one or more embodiments, the lateral fixed portions 82 are at different positions in the lateral direction W. That is, the lateral fixed portion 82 (861) at the center in the longitudinal direction Z is positioned away from the lateral fixed portion 82 (871), which is on the outer side in the longitudinal direction Z, toward the outer side in the lateral direction W.

The contraction portion 83 may be arranged straddling the region between the tail hole 70 and the absorbent core 30. In other words, the contraction portion 83 may be arranged at a position that is away from the stomach-side end edge of the tail hole 70 toward the stomach side and away from a rear-side end edge 30R of the absorbent core 30 toward the rear side. The contraction portion 83 may overlap the region interposed between the tail hole 70 and the absorbent core 30. Alternatively, the contraction portion 83 may overlap the region extending in the lateral direction W from the region interposed between the tail hole 70 and the absorbent core 30, without overlapping the region interposed between the tail hole 70 and the absorbent core 30. According to this configuration, the region between the tail hole 70 and the absorbent core 30 contracts by the contraction portion 83, and the stomach-side end edge of the tail hole 70 is pulled toward the absorbent core 30, which makes it easy for the tail hole 70 to open. As a result, the user can easily notice the presence of the tail hole 70 and can properly insert the tail into the tail hole 70. Furthermore, the tail hole 70 and the absorbent core 30 are spaced apart in the longitudinal direction Z, and the contractive force generated by the contraction portion easily acts on the tail hole 70 without being affected by the stiffness of the absorbent core 30. Therefore, it is easy to obtain an effect of making the opening of the tail hole 70 readily fitted to the tail when a pet is in the diaper. Furthermore, particularly in the case of a cat, the distance between the tail hole 70 and the excretion opening is short. Therefore, in a case where the region between the tail hole and the absorbent core 30 is too long, leakage is likely to occur. In addition, because the absorbent core 30 is not arranged in the region between the tail hole 70 and the absorbent core 30, leakage is likely to occur. However, the contraction by the contraction portion 83 enables the region between the absorbent core 30 and the tail hole 70 to be fitted or can shorten the length of the longitudinal direction Z, which makes it possible to suppress leakage.

The stomach-side end edge of the contraction portion 83 may coincide with the stomach-side end edge of the absorbent core 30, may be away from the stomach-side end edge of the fastening tape 90 toward the rear side and away from the rear-side end edge of the fastening tape 90 toward the stomach side, or may be away from the stomach-side end edge of the leg opening portion toward the stomach side. The stomach-side end edge of the contraction portion 83 is spaced apart from the inner end edge 87F of the second fixed portion 87 positioned on the stomach side, and is positioned away from the inner end edge 87F of the second fixed portion 87, which is positioned on the stomach side, toward the rear side. The non-contraction portion 84 is provided between the inner end edge 87F of the second fixed portion 87 positioned on the stomach side and the contraction portion 83. The rear-side end edge of the contraction portion 83 may be away from the rear-side end edge of the tail hole 70 toward the rear side. An inner edge 831 of the contraction portion 83 may be away from the outer edge of the tail hole 70 toward the inner side in the lateral direction W, or may be away from the outer edge of the absorbent core 30 toward the inner side in the lateral direction W. The rear-side end edge of the contraction portion 83 is spaced apart from the inner end edge 87F of the second fixed portion 87 positioned on the rear side, and may be away from the inner end edge 87F of the second fixed portion 87, which is positioned on the rear side, toward the rear side. The lateral fixed portion 82 (871) on the outer side in the longitudinal direction Z may be away from an outer edge 30E of the absorbent core 30 toward the inner side in the lateral direction W. The lateral fixed portion 82 (861) at the center in the longitudinal direction Z may be away from the outer edge 30E of the absorbent core 30 toward the outer side in the lateral direction W.

The contraction portion 83 may also be arranged in a hole side region R70 that extends outwards in the lateral direction W from the tail hole 70. That is, the contraction portion 83 may also be arranged at a position away from the stomach-side end edge of the tail hole 70 toward the rear side. The hole side region R70 is a concept including a first side region R71 that extends outwards in the lateral direction W from the hole body portion 71 and a second side region R72 that extends outwards in the lateral direction W from the notch portion 72. Because the contraction portion 83 is arranged in the hole side region R70, the tail hole 70 is deformed in a closing direction by the leak-proof gather 80. By pulling the diaper in the longitudinal direction Z when putting the diaper on a pet, the user can easily notice the presence of the tail hole 70. In addition, because the tail hole 70 is deformed in a closing direction and automatically opens when the diaper is put on a pet, it is easy to insert the tail into the tail hole 70 when putting the diaper on a pet.

The contraction portion 83 may have a high contraction portion 881, 882 and a low contraction portion 89 that has a weaker contractive force in the longitudinal direction Z compared to the high contraction portion 881, 882. The low contraction portion may be arranged in at least a part of the hole side region R70. The high contraction portion 881, 882 may be arranged on two outer sides of the hole side region R70 in the longitudinal direction Z. Because the low contraction portion 89 is arranged in the hole side region R70, the tail hole 70 is not excessively deformed in a closing direction by the leak-proof gather 80, which makes it easy for the user to notice the presence of the tail hole 70 when putting the diaper on a pet. In addition, because the tail hole 70 is not excessively deformed in a closing direction, it is easy to insert the tail into the tail hole 70 when putting the diaper on a pet. Furthermore, because the high contraction portion 881, 882 is arranged on two outer sides of the hole side region R70 in the longitudinal direction Z, a force that contracts the low contraction portion 89 arranged in the hole side region R70 in the longitudinal direction Z acts, which makes it easy for the opening of the tail hole 70 to be fitted to the tail when a pet is in the diaper. Therefore, the hole side region R70 is inhibited from excessively contracting in the longitudinal direction Z, and the opening of the tail hole 70 is readily fitted to the tail when a pet is in the diaper.

The high contraction portion 881, 882 may have a stomach-side high contraction portion 881 that is away from the low contraction portion 89 toward the stomach side, and a rear-side high contraction portion 882 that is away from the low contraction portion 89 toward the rear side. The length of the stomach-side high contraction portion 881 in the longitudinal direction Z may be greater than the length of the rear-side high contraction portion 882 in the longitudinal direction Z. Urine is more likely to be discharged to the region on the stomach side of the tail hole 70 than to the region on the rear side of the tail hole 70. In a case where the stomach-side high contraction portion 881 is long enough in the longitudinal direction Z, the region on the stomach side of the tail hole 70 is provided with a long contraction portion 83, which makes it possible to suppress lateral leakage of a body fluid. Incidentally, the rear-side high contraction portion 882 is also arranged in the region on the rear side of the tail hole 70. The rear-side high contraction portion 882 makes the diaper fitted well to the rear side. Therefore, the entire diaper can cover the pet's body, which makes it possible to suppress leakage. In a case where the rear-side high contraction portion 882 is too long in the longitudinal direction Z, because the absorbent core 30 is not arranged, there is a risk that excessive contraction may occur. However, because the rear-side high contraction portion 882 is relatively short in the longitudinal direction Z, the phenomenon can be suppressed where the fastening tape 90 is fastened to wrong positions (positions away from proper positions toward the rear side) due to the excessive contraction caused by the rear-side high contraction portion 882 when the diaper is put on a pet. The stomach-side high contraction portion 881 may be continuously arranged from the stomach-side end edge of the contraction portion 83 to the low contraction portion 89, and the rear-side high contraction portion 882 may be continuously arranged from the rear-side end edge of the contraction portion 83 to the low contraction portion 89. The boundary between the stomach-side high contraction portion 881 and the low contraction portion 89, and the boundary between the rear-side high contraction portion 882 and the low contraction portion 89 may be arranged in the hole side region R70.

In the pet diaper that is in a stretched state, the lateral fixed portion 82 (871) in the hole side region R70 may be positioned away from the lateral fixed portion 82 (861), which is in a region away from the rear-side end edge of the absorbent core 30 toward the stomach side, toward the inner side in the lateral direction W. More specifically, the inner edge 871 of the second fixed portion 87 configures the lateral fixed portion 82 in the hole side region R70, and the inner edge 861 of the first fixed portion 86 configures the lateral fixed portion 82 that is in a region away from the rear-side end edge of the absorbent core 30 toward the stomach side. The absorbent core 30 is arranged in a region that is away from the rear-side end edge of the absorbent core 30 toward the stomach side. Because the lateral fixed portion in this region is positioned relatively on the lateral outer side, the rising portion 81 on the sides of the absorbent core 30 is high enough, which makes it possible to suppress lateral leakage. In addition, because the lateral fixed portion 82 in the hole side region R70 is positioned relatively on a lateral inner side, the rising portion 81 on the sides of the tail hole 70 is inhibited from rising too high. Therefore, when the diaper is put on a pet, the tail hole 70 is inhibited from being excessively deformed by the contraction of the rising portion 81, which makes it easier to insert the tail into the tail hole 70 when putting the diaper on a pet.

The leak-proof elastic member 13 may be cut at the low contraction portion 89 but not cut at the high contraction portion 881, 882 and continuously arranged. That is, the low contraction portion 89 may be a portion where the cut leak-proof elastic member 13 is arranged. According to the above configuration, continuously arranging the stretched leak-proof elastic member 13 and then partially cut the leak-proof elastic member 13 makes it possible to easily provide the low contraction portion 89. In a case where the portion where the cut leak-proof elastic member 13 is arranged configures the low contraction portion 89, a region that extends 5 mm in the longitudinal direction Z from a cutting position CP of the leak-proof elastic member 13 can be defined as the low contraction portion 89, and a region outside the aforementioned region that extends 5 mm from the cutting position CP can be defined as the high contraction portion 881, 882. In addition, the stretch rate of the leak-proof elastic member 13 may be varied so that the low contraction portion 89 and the high contraction portion 881, 882 are provided. The region where the leak-proof elastic member 13 having a high stretch rate is arranged configures the high contraction portion 881, 882, and the region where the leak-proof elastic member 13 having a low stretch rate is arranged configures the low contraction portion 89. The stretch rate can be calculated by stretch rate=(length of leak-proof elastic member 13 in natural state)/(length of leak-proof elastic member 13 in stretched state).

In the low contraction portion 89, the side sheet (leak-proof sheet) 12 may be cut together with the leak-proof elastic member 13. Because the leak-proof sheet is cut at the low contraction portion 89, the user can easily recognize the cutting position CP of the side sheet 12 by seeing the pet diaper from the outside and can easily notice the position or presence of the low contraction portion 89.

The cutting position CP of the leak-proof elastic member 13 may be arranged on the stomach side with respect to the center of the hole side region R70 in the longitudinal direction Z. Due to the stomach-side high contraction portion, the region on the stomach side with respect to the center of the hole side region R70 in the longitudinal direction Z more easily contracts in the longitudinal direction Z, compared to the region on the rear side with respect to the center of the hole side region R70 in the longitudinal direction Z. However, the cutting position of the leak-proof elastic member 13 is arranged at a position that is away from the center of the hole side region R70 in the longitudinal direction Z toward the stomach side. The region on the stomach side with respect to the center of the hole side region R70 in the longitudinal direction Z can be inhibited from excessively contracting due to the influence of the cut leak-proof elastic member 13. Therefore, when the diaper is put on a pet, the tail hole 70 is inhibited from being excessively deformed within the entire hole side region R70, which makes it easy to obtain an effect of more easily inserting the tail into the tail hole 70 when putting the diaper on a pet. The cutting position CP of the leak-proof elastic member 13 may be arranged at a position that is away from the center of the first side region R71 in the longitudinal direction Z toward the rear side. The vicinity of the rear-side end portion of the hole body portion 71 contracts weakly, which makes it possible to inhibit the rear-side end edge (the apex of the protruding portion) of the hole body portion 71 from coming into tight contact with the upper side of the pet's tail.

The low contraction portion 89 may be arranged in a region (first side region) R71 that extends outwards in the lateral direction W from the hole body portion 71. In this case, the hole body portion 71 is not excessively deformed in a closing direction by the leak-proof gather 80, which makes it easy for the user to notice the presence of the hole body portion 71 when putting the diaper on a pet. In addition, because the hole body portion 71 is not excessively deformed in a closing direction, it is easy to insert the tail into the tail hole 70 when putting the diaper on a pet. In one or more embodiments, in the pet diaper that is in a stretched state, the cutting position CP is provided in a region which overlaps the notch portion 72 but does not overlap the hole body portion 71. More specifically, the cutting position CP may be a region that overlaps the notch portion 72 arranged in the first side region R71.

In the pet diaper that is in a stretched state, the leak-proof gather 80 may be arranged in a region that overlaps the notch portion 72 but does not overlap the hole body portion 71. The hole body portion 71 is unlikely to be covered with the leak-proof gather 80, which makes it easy to secure the visibility of the hole body portion 71. As a result, the user can easily notice the presence of the tail hole 70.

Hitherto, the present invention has been described in detail using the above-described embodiments, but it is obvious to those skilled in the art that the present invention is not limited to the embodiments described in the present specification. The present invention can be carried out as a correction and modification aspect within the gist and scope of the present invention defined by the description of the claims. Therefore, the description of the present specification is intended for exemplary description and does not mean to limit the present invention by any means.

The entire contents of Japanese Patent Application No. 2020-038779 filed on Mar. 6, 2020 are incorporated into the present specification by reference.

According to one or more embodiments, a pet diaper that makes it easy to properly insert a tail into a tail hole when putting the diaper on a pet can be provided.

Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

REFERENCE SIGNS LIST

1: pet diaper, 2: main body portion, 10: top sheet, 11: center sheet, 12: side sheet, 13: leak-proof elastic member, 20: back-surface sheet, 30: absorbent core, 70: tail hole, 71: hole body portion, 80: leak-proof gather, 81: raising portion, 82: lateral fixed portion, 83: contraction portion, 84: non-contraction portion, 85: longitudinal fixed portion, 881: stomach-side high contraction portion, 882: rear-side high contraction portion, 89: low contraction portion, W: lateral direction, Z: longitudinal direction, R70: hole side region

What is claimed is:
1. A pet diaper having a lateral direction along a waistline direction of a pet and a longitudinal direction that is orthogo- nal to the lateral direction and extends in a direction connecting a stomach side and a rear side of the pet, the pet diaper comprising:
- a main body portion comprising a top sheet, a back-surface sheet, and an absorbent core between the top sheet and the back-surface sheet, wherein
- the main body portion includes an upright leak-proof gather and a tail hole that has a hole body portion through which a tail of the pet is to be inserted,
- the leak-proof gather includes a rising portion configured to rise up and a first lateral fixed portion that is positioned away from the rising portion toward a lateral outer side of the pet diaper and that functions as a rising fulcrum of the rising portion,
- the rising portion of the leak-proof gather includes a contraction portion that has a leak-proof elastic member linearly extending in the longitudinal direction in a stretched state and not bonded to the back-surface sheet,
- the tail hole is positioned on the rear side and away from an end edge of the absorbent core toward the rear side,
- the contraction portion of the rising portion straddles a region of the pet diaper between the tail hole and the absorbent core,
- the contraction portion of the rising portion is positioned in a hole side region of the pet diaper that extends from the tail hole toward the lateral outer side,
- the contraction portion of the rising portion includes a low contraction portion in at least a part of the hole side region and a high contraction portion on two outer sides of the hole side region in the longitudinal direction, the low contraction portion having a weaker contractive force in the longitudinal direction compared to the high contraction portion,
- the tail hole includes the hole body portion and a notch portion that is a portion to tear the top sheet and the back-surface sheet and that is configured to enlarge a dimension of the hole body portion, and
- the low contraction portion is positioned in a region that extends to the lateral outer side from the hole body portion.

2. The pet diaper according to claim 1, wherein
the high contraction portion includes a stomach-side high contraction portion positioned away from the low contraction portion toward a stomach side and a rear-side high contraction portion positioned away from the low contraction portion toward a rear side, and
in the longitudinal direction, the stomach-side high contraction portion is longer in length than the rear-side high contraction portion.

3. The pet diaper according to claim 1, wherein in the pet diaper in a stretched state, the first lateral fixed portion in the hole side region is positioned away from a second lateral fixed portion, which is in a region that is away from an end edge of the absorbent core on the rear side toward the stomach side, toward a lateral inner side.

4. The pet diaper according to claim 1, wherein the leak-proof elastic member is cut in the low contraction portion and is continuously disposed in the high contraction portion without being cut.

5. The pet diaper according to claim 4, wherein
the leak-proof gather includes the leak-proof elastic member and a leak-proof sheet to which the leak-proof elastic member is joined, and
the leak-proof sheet is cut together with the leak-proof elastic member in the low contraction portion.

6. The pet diaper according to claim 4, wherein a cutting position of the leak-proof elastic member is positioned on the stomach side with respect to a longitudinal center of the hole side region.

7. The pet diaper according to claim 1, wherein in the pet diaper in a stretched state, the leak-proof gather is disposed in a region that overlaps the notch portion but does not overlap the hole body portion.

8. A pet diaper having a lateral direction along a waistline direction of a pet and a longitudinal direction that is orthogonal to the lateral direction and extends in a direction connecting a stomach side and a rear side of the pet, the pet diaper comprising:
- a main body portion comprising a top sheet, a back-surface sheet, and an absorbent core between the top sheet and the back-surface sheet, wherein
- the main body portion includes an upright leak-proof gather and a tail hole that has a hole body portion through which a tail of the pet is to be inserted,
- the leak-proof gather includes;
  - a rising portion configured to rise up;
  - a lateral fixed portion that is positioned away from the rising portion toward a lateral outer side of the pet diaper and that functions as a rising fulcrum of the rising portion; and
  - a longitudinal fixed portion that is positioned away from the rising portion toward the lateral outer side in the longitudinal direction and that functions as a rising fulcrum of the rising portion,
- the rising portion of the leak-proof gather includes a contraction portion that has a leak-proof elastic member linearly extending in the longitudinal direction in a stretched state and not bonded to the back-surface sheet,
- the tail hole is positioned on the rear side and away from an end edge of the absorbent core toward the rear side,
- the contraction portion of the rising portion straddles a region of the pet diaper between the tail hole and the absorbent core,
- the contraction portion of the rising portion is positioned in a hole side region of the pet diaper that extends from the tail hole toward the lateral outer side,
- a rear-side end edge of the contraction portion is positioned on a rear side of an inner edge of the longitudinal fixed portion which is positioned rear side, and
- the inner edge of the longitudinal fixed portion is positioned on the stomach side of a stomach edge of the hole side region.

9. A pet diaper having a lateral direction along a waistline direction of a pet and a longitudinal direction that is orthogonal to the lateral direction and extends in a direction connecting a stomach side and a rear side of the pet, the pet diaper comprising:
- a main body portion comprising a top sheet, a back-surface sheet, and an absorbent core between the top sheet and the back-surface sheet, wherein
- the main body portion includes an upright leak-proof gather and a tail hole that has a hole body portion through which a tail of the pet is to be inserted,
- the leak-proof gather includes a rising portion configured to rise up and a lateral fixed portion that is positioned away from the rising portion toward a lateral outer side of the pet diaper and that functions as a rising fulcrum of the rising portion,
- the rising portion of the leak-proof gather includes a contraction portion that has a leak-proof elastic member linearly extending in the longitudinal direction in a stretched state and not bonded to the back-surface sheet, the tail hole is positioned on the rear side and away from an end edge of the absorbent core toward the rear side, the contraction portion of the rising portion straddles a region of the pet diaper between the tail hole and the absorbent core, and the leak-proof elastic member is cut, wherein a cutting position of the leak-proof elastic member is positioned in a hole side region that extends from the tail hole toward the lateral outer side of the pet diaper.

10. A pet diaper having a lateral direction along a waistline direction of a pet and a longitudinal direction that is orthogonal to the lateral direction and extends in a direction connecting a stomach side and a rear side of the pet, the pet diaper comprising:

a main body portion comprising a top sheet, a back-surface sheet, and an absorbent core between the top sheet and the back-surface sheet, wherein the main body portion includes an upright leak-proof gather and a tail hole that has a hole body portion through which a tail of the pet is to be inserted, the leak-proof gather includes a rising portion configured to rise up and a lateral fixed portion that is positioned away from the rising portion toward a lateral outer side of the pet diaper and that functions as a rising fulcrum of the rising portion, the rising portion of the leak-proof gather includes a contraction portion that has a leak-proof elastic member linearly extending in the longitudinal direction in a stretched state and not bonded to the back-surface sheet, the tail hole is positioned on the rear side and away from an end edge of the absorbent core toward the rear side, the contraction portion of the rising portion straddles a region of the pet diaper between the tail hole and the absorbent core, the tail hole includes the hole body portion and a notch portion, and in a plane view, the contraction portion overlaps the notch portion, straddles the notch portion, and extends in the longitudinal direction.

11. The pet diaper according to claim 10, wherein the notch portion is configured to be apart from the hole body portion.

\* \* \* \* \*